United States Patent
Mouhasseb

(10) Patent No.: US 7,017,396 B2
(45) Date of Patent: Mar. 28, 2006

(54) METHOD AND DEVICE FOR THE DETERMINATION OF AT LEAST ONE PARAMETER OF A MIXTURE OF A SUPPORT, WATER AND GAS

(75) Inventor: Haissam Mouhasseb, Glärnischstrasse 8, CH-8117 Pfaffhausen (CH)

(73) Assignee: Haissam Mouhasseb, Pfaffhausen (CH)

( * ) Notice: Subject to any disclaimer, the term of this patent is extended or adjusted under 35 U.S.C. 154(b) by 0 days.

(21) Appl. No.: 10/312,283

(22) PCT Filed: Jun. 19, 2001

(86) PCT No.: PCT/EP01/06898

§ 371 (c)(1),
(2), (4) Date: Jul. 16, 2003

(87) PCT Pub. No.: WO01/98777

PCT Pub. Date: Dec. 27, 2001

(65) Prior Publication Data

US 2004/0025574 A1 Feb. 12, 2004

(30) Foreign Application Priority Data

Jun. 21, 2000 (DE) ................................ 100 30 602

(51) Int. Cl.
*G01N 25/56* (2006.01)
*G01R 27/04* (2006.01)

(52) U.S. Cl. ........................... 73/73; 324/640; 324/643

(58) Field of Classification Search .................... 73/73, 73/61.41; 324/640, 643
See application file for complete search history.

(56) References Cited

U.S. PATENT DOCUMENTS 4,700,140 A * 10/1987 Fertl ........................... 324/338

(Continued)

FOREIGN PATENT DOCUMENTS

| DE | 19652679 | 4/1998 | |
| GB | 2313443 | 11/1997 | |
| JP | 6107051 A | * 1/1986 | .................... 73/73 |

OTHER PUBLICATIONS

English language translation of DE 196 52 679 C1.*
Kiran Pokkuluri; "Effects of Admixtures, Chlorides, and Moisture on . . . Range"; Oct. 1998.

(Continued)

*Primary Examiner*—Michael Cygan
(74) *Attorney, Agent, or Firm*—Ladas & Parry

(57) ABSTRACT

In order to measure at least one parameter of a mixture of carrier substance, water and gas, the permittivity value of the mixture is measured at different frequencies by means of a network analyzer (1) and a sensor. The measurements are entered into a mixing formula for forming a system of equations. From the system of equations, at least one parameter of the mixture can be determined. The method is also suited for the measurement of the location dependence of a parameter, e.g. for the measurement of the humidity distribution in concrete.

5 Claims, 1 Drawing Sheet

U.S. PATENT DOCUMENTS

| | | | | |
|---|---|---|---|---|
| 4,703,277 | A | * | 10/1987 | Kenyon et al. ............. 324/323 |
| 4,866,371 | A | * | 9/1989 | De .............................. 324/639 |
| 5,059,907 | A | * | 10/1991 | Sherman ..................... 324/323 |
| 5,363,052 | A | * | 11/1994 | McKee ....................... 324/663 |
| 5,418,466 | A | | 5/1995 | Watson et al. |
| 5,420,589 | A | * | 5/1995 | Wells et al. .................. 342/22 |
| 6,147,503 | A | | 11/2000 | Nelson et al. ............... 324/637 |
| 6,246,354 | B1 | * | 6/2001 | Liedtke et al. ................ 342/22 |
| 6,614,240 | B1 | * | 9/2003 | Zoughi et al. .............. 324/646 |
| 6,691,563 | B1 | * | 2/2004 | Trabelsi et al. ................ 73/73 |

OTHER PUBLICATIONS

Nassar E.M. etal; "A Probe Antenna for In Situ Measurement . . . Materials" IEEE Transactions on Antennas and Propagation; vol. 47, No. 6, Jun. 1999; pp1085-1092.

Adiseshu Nyshadham et al; "Permittivity Measruement Using Open-Ended . . . Analysis" IEEE Transactions on Microwave Theory and Techniques; Vo. 40; No. 2; Feb. 1992 pp 305-314.

* cited by examiner

METHOD AND DEVICE FOR THE DETERMINATION OF AT LEAST ONE PARAMETER OF A MIXTURE OF A SUPPORT, WATER AND GAS

CROSS REFERENCE TO RELATED APPLICATIONS

This application claims the priority of German patent application 100 30 602.0, filed Jun. 21, 2000, the disclosure of which is incorporated herein by reference in its entirety.

BACKGROUND

The invention relates to a method and a device according to the preamble of the independent claims where at least one parameter of a mixture is to be determined, the components of which mixture comprise a carrier substance, water and gas.

A method of this type can in particular be used for determining the humidity state of concrete elements. The knowledge of the humidity state of concrete elements is often indispensable for avoiding or assessing of damages, but also for carrying out building and renovation steps. Furthermore, the humidity situation has to be known when laying floors (tiles, parquets, etc) in lofts, when coating concrete surfaces, and when assessing the corrosion of rebars. Hence, the measurement of humidity is of particular importance in concrete construction as well.

Methods of this type can, however, also be used in other fields, such as in the characterisation of pharmaceuticals and food stuff, and wherever a parameter of a mixture of carrier substance, water and gas has to be determined, wherein the carrier substance can be solid or liquid.

In order to keep expense and costs small, a corresponding method should be non-destructive.

A method and a device for determining the humidity content of porous building materials have been known from the patent DE 196 52 679 C1. There, the humidity of the mixture is determined by feeding electromagnetic waves of several frequencies to a sensor and by determining the frequency dependent permittivity value of the mixture by means of calibration data specifically provided for the sensor. By means of a system of equations, based on the mixing formula of Polder-van Santen/de Loor, which is solved for the frequency independent parameters, the volume fraction of the liquid water can be determined.

It has been found, however, that the accuracy of this method is limited.

SUMMARY OF THE INVENTION

Hence, it is a general object of the invention to provide a method and a device of the type mentioned above that allow measurements of a higher accuracy.

In a first aspect of the invention, the permittivity value of the bound water is entered into the mixing formula as a frequency dependent function. It has been found that a more realistic model of the system is achieved by this step and the measurement accuracy is improved.

In a second aspect of the invention, it is assumed that the contribution of the bound water does not have to be taken into account separately. In this case, the following parameters (or values derived from these parameters) are determined simultaneously from the system of equations:

volume fraction $v_1$ of the gas, volume fraction $v_2$ of the free water, at least one of the depolarization factors $N_{2j}$ of the free water and the conductivity of the free water.

With other words, these parameters are therefore all fitted to the measured values, e.g. by calculus of observations, which provides a better modelling of the system and therefore a higher accuracy of measurement.

Any formula describing the permittivity value of the mixture in dependence of the permittivity value of the components and their volume fractions can be used as mixing formula, such as the equation of Polder-van Santen/de Loor mentioned above. Preferably, however, a mixing formula described in the following is used.

A third aspect of the invention relates to the mixing formula. Preferably, a formula as follows is used $$\varepsilon_m = \varepsilon_b + \sum_{i=1}^{n} \frac{v_i}{3} \cdot (\varepsilon_i - \varepsilon_b) \cdot \sum_{j=1}^{3} \frac{\varepsilon_m}{\varepsilon_m + N_{ij} \cdot (\varepsilon_i - \varepsilon_m)}$$

with $\varepsilon_1$ and $v_1$ being the permittivity value and the volume fraction of the gas, $\varepsilon_2$ and $v_2$ the permittivity value and the volume fraction of the free water, $\varepsilon_3$ and $v_3$ the permittivity value and the volume fraction of the bound water (if the same is to be taken account of), $\varepsilon_b$ the permittivity value of the carrier substance, and $N_{1j}$, $N_{2j}$ and $N_{3j}$ the depolarization factors of an ellipsoidal cavity of the gas or the free water or the bound water, respectively, wherein n=3 when taking the bound water into account and n=2 when neglecting the bound water.

If this mixing formula is measured at a sufficient number for frequencies, a sufficiently determined or overdetermined system of equations results, which allows to determine at least one of the unknown parameters, such as the volume fraction of the free water.

In a further aspect of the invention it is taken into account that the water fraction of the mixture, or another parameter to be determined, can vary as a function of the depth, i.e. the distance to the surface of the mixture. In order to take this into account, several measuring steps are carried out, in which the sensor is arranged at a known distance from the mixture and is separated from the same by a dielectric of known permittivity. In each measuring step the sensor determines a value $w_k$ depending on the integral permittivity value $\varepsilon_k$ of the mixture in the measuring range. Then, an evaluation is carried out, in which the depth dependence of the liquid water fraction is determined based on the different dependencies of the values $w_k$ from the parameter to be determined.

BRIEF DESCRIPTION OF THE DRAWINGS

Further embodiments, advantages and applications of the invention result from the dependent claims and from the now following description with reference to the figures, wherein:

DETAILED DESCRIPTION OF THE INVENTION

Figure 1:
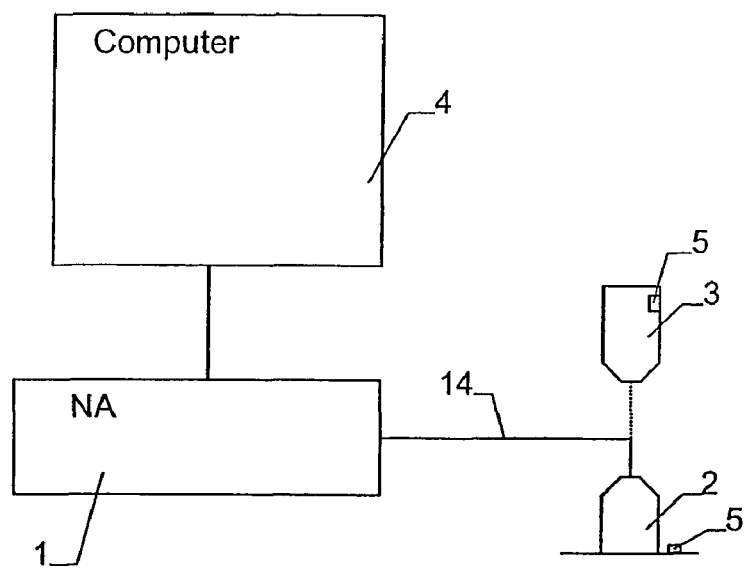
FIG. 1 is a schematic set-up of a preferred embodiment of the invention.

The set-up of FIG. 1 comprises a permittivity value measuring apparatus 1 for a frequency dependent determination of the complex permittivity value of a mixture. Further, it comprises a surface sensor 2 for measuring solid mixtures, which can be placed against a smooth and flat surface, and a circular hollow waveguide sensor 3 for measuring liquid mixtures, which can be filled into sensor 3. The sensors 2 or 3 are electrically connected in selectable manner to the permittivity value measuring device 1 via a coaxial transmission line 14. The permittivity value measuring device 1 comprises a vector network analyzer, which measures the real and imaginary part of the reflection factor of the used sensor. This reflection factor is converted to a complex permittivity $\epsilon_m$ of the mixture by means of sensor specific calibration data. Corresponding methods are known to the person skilled in the art.

For evaluating the measurements, a data processing system 4, such as a conventional PC, is connected to the permittivity value measuring device 1 and controls the whole measuring and calculation process in the manner described in the following. A temperature sensor 5 serves to detect the temperature of the mixture to be examined.

Figure 2:
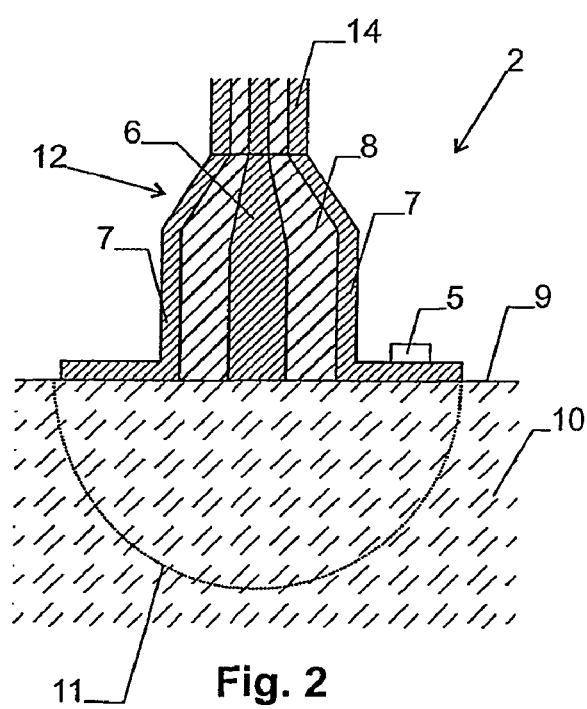
FIG. 2 is a sectional view of a surface sensor.

FIG. 2 shows a sectional view through the surface sensor 2. It has a rotationally symmetric design with an inner conductor 6 and an outer conductor 7, which are separated by a coaxial isolation layer 8, preferably of Teflon. On its measuring end, the temperature sensor 5 is arranged.

The surface sensor 2 can be placed against the smooth, flat surface 9 of the mixture 10 to be measured, such that its measuring range 11 extends into the mixture. As described further below, it can also be arranged at a distance from the mixture 10 to be measured such that its measuring range 11 extends only partially into the mixture.

On a side facing the coaxial transmission line 14, the surface sensor 2 has a tapered transition section 12. It guarantees a impedance matched connection of the surface sensor 2 to the coaxial line 14. The transition is formed by two cones with common tip. In such a geometry, the impedance and the cone angles are connected via the following relation:

$$Z_0 = \frac{Z_{F0}}{2\pi\sqrt{\epsilon_C}} \ln\frac{\tan(\vartheta_2/2)}{\tan(\vartheta_1/2)} \quad (1)$$

Herein, $Z_0$ is the impedance of the transition section (which is to be equal to the one of the coaxial cable and should e.g. be 50 Ohms), $Z_{F0}$ the vacuum impedance ($Z_{F0}=\sqrt{\mu_0/\epsilon_0}=377$ Ohm), $\epsilon_c$ the permittivity of the isolation layer 8, $\theta_1$ the angle of the inner cone of the inner conductor 6 and $\theta_2$ the angle of the outer cone of the outer conductor 7.

Figure 3:
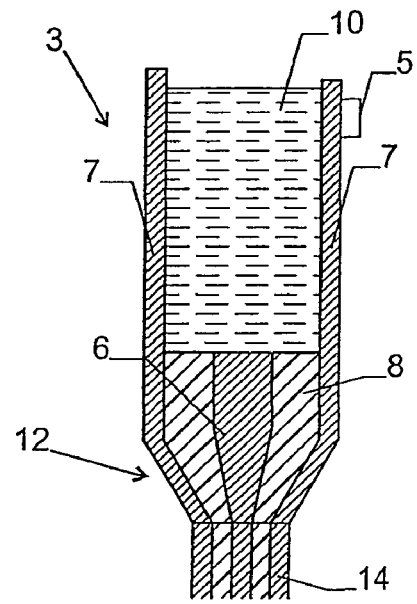
FIG. 3 is a sectional view of a hollow wave guide sensor.

FIG. 3 shows a sectional view of the hollow wave guide sensor 3. It again has a rotationally symmetric design with an inner conductor 6 and an outer conductor 7, which are separated by a coaxial isolation layer 8, preferably of Teflon. The outer conductor 7 extends beyond the isolation layer and the inner conductor and limits a cavity for receiving the mixture 10 to be measured. Again, a transition section 12 for an impedance matched connection with the coaxial transmission line 14 can be provided.

Wit the sensors according to FIGS. 2 and 3 the permittivity is determined via the reflection of an electromagnetic wave. The permittivity can, however, also be measured in a transmission measurement, where e.g. the damping and phase shift of an electromagnetic wave upon transition through the mixture is measured. In that case the sensor consists of a sender and a receiver. Corresponding techniques are known to the person skilled in the art.

The mixture to be measured can, as already mentioned, be in solid or liquid form. It comprises a carrier substance (preferably liquid or solid concrete), which forms the predominant volume fraction of the mixture, as well as water and gas, which are e.g. arranged in pores or cavities in the carrier substance.

For measuring at least one parameter of this mixture, we proceed as follows.

In a first step, the mixture 10 is brought into the measuring range of the sensor 2 or 3, respectively. Then, its temperature T is measured by means of temperature sensor 5.

Now, the complex permittivity value $\epsilon_m$ of the mixture within the measuring range 11 is determined by means of the permittivity value measuring device 1, namely at several measuring frequencies $f_i$, preferably in a range between 10 kHz and 10 GHz, preferably 10 MHz and 1 GHz.

These measurements are compared to a theoretical formula based on a model of the mixture, preferably:

$$\epsilon_m = \epsilon_b + \sum_{i=1}^{n} \frac{v_i}{3} \cdot (\epsilon_i - \epsilon_b) \cdot \sum_{j=1}^{3} \frac{\epsilon_m}{\epsilon_m + N_{ij} \cdot (\epsilon_i - \epsilon_m)} \quad (2)$$

Here, $\epsilon_1$ and $v_1$ designate the permittivity value and volume fraction of the gas, $\epsilon_2$ and $v_2$ the permittivity value and volume fraction of the free water, $\epsilon_3$ and $v_3$ the permittivity value and volume fraction of the bound water, $\epsilon_b$ the permittivity value of the carrier substance and $N_{1j}$, $N_{2j}$ and $N_{3j}$ the depolarization factors of an ellipsoidal cavity of the gas or the free water or the bound water, respectively. If the contributions of the bound water are taken into account, n is equal to 3. If these contributions are neglected, n is equal to 2.

By entering the measured value $\epsilon_m(f_i)$ into equation (2) a system of equations is obtained. If a sufficient number of measurement values is available, an evaluation of the system of equations allows to determine different parameters of the mixture, as it is described in the following. Preferably, the number of measurements is chosen to be so high that the system of equations is overdetermined and the parameters can be determined by calculus of observations with high accuracy.

It is to be noted that besides equation (2) other approaches and approximations exist that estimate the permittivity value $\epsilon_m$ of a mixture. One other equation, described in DE 196 52 679, is the mixing formula of Polder-van Santen/de Loor. Furthermore, various approximations can e.g. be used for the depolarization factors. For example, by assuming rotational symmetry for the depolarization factors of the free water, the following approximations can be used:

$$N_{21}=N_{22}=N_{fw}$$

$$N_{23}=1-2\cdot N_{fw}, \quad (3)$$

i.e. the depolarization effects in the cavities of the free water can be expressed by a single parameter $N_{fw}$.

For the depolarization factors of gas, the following assumption is found to be reasonable:

$$N_{11}=N_{12}=N_{13}=1/3 \quad (4)$$

For the depolarization factors of the bound water, the following approximation can be used:

$$N_{31}=N_{32}=0 \text{ and } N_{33}=1. \quad (5)$$

In general, the mixing formula have, when the contribution of bound water is taken into account, the following form $$\epsilon_m=\epsilon_m(\epsilon_1, \epsilon_2, \epsilon_3, \epsilon_b, v_1, v_2, v_3), \quad (6)$$

i.e. the permittivity value of the mixture is given as a function of the permittivity values of the components and the volume fractions. Where applicable, further parameters can be taken into account as unknowns in equation (6), such as at least one depolarization factor of a component of the mixture, in particular a depolarization factor of free water, e.g. the depolarization factor $N_{fw}$ of equation (3).

If the contribution of the bound water is not taken into account or neglected (or, taken into account in approximation as a constant contribution to the permittivity value $\epsilon_b$ of the carrier substance), and if approximations of the type of equations (3), (4) and (5) are used for the depolarization factors, it results:

$$\epsilon_m=\epsilon_m(\epsilon_1, \epsilon_2, \epsilon_b, v_1, v_2, N_{fw}). \quad (7)$$

Some of the parameters in equations (2), (6) or (7) can be estimated with sufficient accuracy, while others can only be determined by the measurement.

The permittivity value $\epsilon_1$ of the gas at the used frequencies can be set to 1+0·i in good approximation.

For the permittivity value $\epsilon_2$ of the free water the Cole-Cole approximation can be used:

$$\varepsilon_2(f) = \varepsilon_{\infty(fw)} + \frac{\varepsilon_{stat(fw)} - \varepsilon_{\infty(fw)}}{1+(i\cdot\omega\cdot\tau_{fw})^{1-\alpha}} - i\cdot\frac{\sigma_{fw}}{\omega\cdot\varepsilon_o}, \quad (8)$$

with the parameters $\epsilon_{stat(fw)}$, $\epsilon_{\infty(fw)}$, $\tau_{fw}$, $\alpha$, and $\sigma_{fw}$, wherein $\epsilon_O=8.8642\times10^{-12}$ F/m and $\omega=2\pi f$. $\epsilon_{stat(fw)}$ corresponds to the static dielectric constant of free water, $\epsilon_{\infty(fw)}$ to the dielectric constant of free water at optical frequencies, $\tau_{fw}$ to the relaxation time of free water, $\alpha=0.02$ and $\sigma_{fw}$ to the conductivity of free water. Numerical, temperature and salt dependent values of the corresponding parameters are published in "Permittivity Measurements Using Open-Ended Sensors and Reference Liquid Calibration—An Uncertainty Analysis", by A. Nyshadham et al., IEEE Transactions on Microwave Theory and Techniques, Vol. 40(2), pp. 305ff, 1992.

For the permittivity value $\epsilon_3$ of the bound water, the Cole-Cole approximation can be used as well:

$$\varepsilon_3(f) = \varepsilon_{\infty(bw)} + \frac{\varepsilon_{stat(bw)} - \varepsilon_{\infty(bw)}}{1+(i\cdot\omega\cdot\tau_{bw})^{1-\alpha}} - i\cdot\frac{\sigma_{bw}}{\omega\cdot\varepsilon_o}, \quad (9)$$

with the parameters $\epsilon_{stat(bw)}$, $\epsilon_{\infty(bw)}$, $\tau_{bw}$, $\alpha$, and $\sigma_{bw}$ and with $\epsilon_O=8.8642\times10^{-12}$ F/m and $\omega=2\pi f$. Preferably, the following values are used:

$$\epsilon_{stat(bw)}\approx 80,$$

$$\epsilon_{\infty(bw)}\approx 4.5,$$

$$\tau_{bw}\approx-7.721\times10^{-14}T^3+1.017\times10^{-11}T^2 31\ 5.516\times 10^{-10}T+1.645\times10^{-8} \text{ seconds (temperature T in } ^\circ\text{C.)},$$

$$\alpha\approx 0, \text{ and}$$

$$\sigma_{bw}\approx 0.$$

The permittivity value $\epsilon_b$ of the carrier substance is generally known from calibration measurements.

The volume fractions $v_1$, $v_{23}$ and $v_3$ give, when added, the porosity of the carrier substance. If the contribution of the bound water is not taken into account, $v_3$ can be set to zero. In many practical applications, the volume fraction $v_3$ is a fixed quantity, because bound water is always present in the carrier substance and is hard to remove. For concrete, $v_3$ has a value of approximately 0.016.

From equation (7) (or equation (2) respectively, with $v_3=0$ and the approximations (3) and (5)) a system of equations results when at least four measuring values at different frequencies are evaluated and the above values for the known parameters are used, which system of equations allows the simultaneous determination of the following unknown parameters:

volume fraction $v_1$ of the gas, volume fraction $v_2$ of the free water, at lest one of the depolarization factors $N_{2j}$ of the free water, in particular $N_{fw}$ when using the approximation (4), and electric conductivity of the free water.

Instead of these parameters, other values depending on these parameters can be determined. In particular, the salt contents of the free water can e.g. be determined from the conductivity of the free water by using empirical equations according to the above mentioned publication of A. Nyshadham et al. Corresponding conversion formulas are known to the person skilled in the art.

If the contribution of the bound water is not neglected and taken account of explicitly, the number of the unknown parameters increases. It is found, however, that it is still possible to make an accurate measurement when a good estimate for the permittivity value $\epsilon_3$ is used. For this purpose it is important that it is taken into account that this permittivity value $\epsilon_3$ is frequency dependent at the used measuring frequencies, i.e. in general $\epsilon_3=\epsilon_3(f)$. For example, equation (9) can be used as specific formula. Depending on the frequency range, the real value of equation (9) can be set to a constant value of e.g. 4.5. In particular, as mentioned before, it can be said in good approximation that, at the given frequency, the conductivity $\sigma_{bw}$ of the bound water is zero.

Hence, when taking the contributions of the free water into account, at least one parameter, in particular the volume fraction $v_2$ of the free water, can be determined from equation (2) or (5) when entering the measuring values into the system of equations.

With the method described above, it is also possible to determine the porosity of the carrier substance as a sum of the volume fractions $v_1+v_2$ (or $v_1+v_2+v_3$ when taking the bound water into account).

Furthermore, the volumetric amount of water can be determined with the present method from the value $v_2$ or the sum $v_2+v_3$. When the pure density of the carrier substance is known and the known or determined porosity is taken into account, the weight fraction of water content can be determined as follows:

$$\rho_{roh} = \rho_{rein} \cdot (1-\theta)$$

with:

| | |
|---|---|
| $\rho_{roh}$ | gross density [e.g. g/cm³] |
| $\rho_{rein}$ | pure density [e.g. g/cm³] |
| $\theta$ | porosity [-] | and:

$$w_{gew.} = \frac{w_{vol.}}{\rho_{roh}}$$

with:

| | |
|---|---|
| $W_{gew.}$ | weight fraction of water content [M. -%] |
| $W_{vol.}$ | volume fraction of water content [vol. -%] |

The pure density can be determined in simple manner in a laboratory by means of standard procedures.

In the above discussion it has been assumed that the permittivity value $\epsilon_m$ of the mixture is position independent. If this is not the case, the measured value $\epsilon_m$ is an average value, i.e. an integral value, of the permittivity of the mixture within the measuring range 11 of the sensor.

In particular for solid mixtures the permittivity value is, however, often a parametric function f of the depth, i.e. of the distance from the surface, for example $$f(x) = a1 + a2 \cdot (1 - \exp(-x/a3)), \quad (9)$$

wherein a1, a2 and a3 are unknown parameters.

It has been found that the present method allows the determination of the depth dependent liquid water fraction, or, analogously, of another depth dependent parameter (such as the salt content).

For this purpose, several measuring steps k are carried out, wherein in each measuring step the sensor is arranged at a known distance from the mixture and is separated from the same by a dielectric of known permittivity. The dielectric can, in particular, also be air, and in one of the measuring steps the distance is preferably 0. Between measuring steps, the distance between the sensor and the mixture is changed, or another dielectric is introduced between the sensor and the mixture. In most measuring steps, the measuring range of the sensor will therefore enter only partially and in differently strong manner into the mixture.

In each measuring step, a value $w_k$ depending on the integral permittivity value $\epsilon_{mk}$ is measured, such as e.g. the water fraction or the salt content. For this purpose, it can e.g. be assumed that the permittivity value $\epsilon_m$ is constant over the measuring range, such that the above evaluations can be used. From the changing dependence of the values $w_k$ from the parameter to be measured (such as the water fraction) in the measuring range, the values a1, a2, a3 and therefore the function f can be determined.

Preferably, the integral $$w_k = \int E_k(x) f_{a1,a2,\ldots}(x) dx \quad (10)$$

is calculated for each measuring step k, wherein $E_k(x)$ is a normalized dependence of the sensitivity of the sensor from the depth x in the mixture in the conditions of measuring step k (distance between sensor and mixture and permittivity of the dielectric).

The dependence $E_k(x)$ can e.g. be determined by previous calibration measurements under the measuring conditions of the measuring step, or numerically, e.g. by finite element calculus.

For example, it can be based on the sensitivity S(x) of the sensor lying against the mixture. If the distance between sensor and mixture in measuring step k is equal to $d_k$ and the permittivity value of the dielectric between sensor and mixture is approximately equal to the average permittivity value of the mixture, we get in approximation:

$$E_k(x) = S(x + d_k) \quad (11)$$

By entering the measuring values $w_k$ in equation (10), it is again possible to set up a system of equations for the parameters a1, a2, a3 . . . , which can be solved by means of the calculus of observations.

While, in the present application, preferred embodiments of the invention are described, it is to be distinctly understood that the invention is not limited thereto and can also be carried out in different manner within the scope of the following claims.

The invention claimed is:

1. A method for determining at least one parameter of a mixture of a carrier substance, water and gas, comprising the following steps:
   bringing the mixture into a measuring range of a sensor,
   measuring complex permittivity values $\epsilon_m(f_i)$ of the mixture at several measuring frequencies $f_i$ by feeding an electromagnetic wave to the sensor and by means of calibration data of the sensor,
   establishing a system of equations by entering the permittivity values $\epsilon_m(f_i)$ into a mixing formula $$\varepsilon_m = \varepsilon_b + \sum_{i=1}^{n} \frac{v_i}{3} \cdot (\varepsilon_i - \varepsilon_b) \cdot \sum_{j=1}^{3} \frac{\varepsilon_m}{\varepsilon_m + N_{ij} \cdot (\varepsilon_i - \varepsilon_m)}$$

with $\epsilon_1$ and $v_1$ being the permittivity value and the volume fraction of the gas, $\epsilon_2$ and $V_2$ the permittivity value and the volume fraction of the free water, $\epsilon_3$ and $v_3$ the permittivity value and the volume fraction of the bound water, $\epsilon_b$ the permittivity value of the carrier substance, and $N_{1j}$, $N_{2j}$ and $N_{3j}$ the depolarization factors of an ellipsoidal cavity of the gas or the free water or the bound water, respectively, wherein n=3 when taking the bound water into account and n=2 when neglecting the bound water, and
determining at least one unknown parameter of the mixing formula, or of a value derived from the unknown parameter, by evaluating the system of equations.

2. The method of claim 1 wherein one of the depolarization factors $N_{2j}$ of the free water is determined from the system of equations.

3. The method of claim 1 wherein for bound water $N_{21}=N_{32}=0$ and $N_{33}=1$ is used.

4. The method of claim 1 wherein for the gas $N_{11}=N_{12}=N_{13}=\frac{1}{3}$ is used.

5. The method of claim 1 wherein $N_{21}=N_{22}=N_{fw}=N_{23}=1-2 \cdot N_{fw}$ is used and the value of $N_{fw}$ is determined from the system of equations.

* * * * *